(12) United States Patent
Lundstrom

(10) Patent No.: US 7,239,154 B2
(45) Date of Patent: Jul. 3, 2007

(54) SOIL PENETRATING ELECTRODE WITH CONICAL TAPER

(76) Inventor: John W. Lundstrom, 603 Crestview Dr., Glendora, CA (US) 91741

( * ) Notice: Subject to any disclaimer, the term of this patent is extended or adjusted under 35 U.S.C. 154(b) by 0 days.

(21) Appl. No.: 10/808,838

(22) Filed: Mar. 24, 2004

(65) Prior Publication Data

US 2004/0207382 A1 Oct. 21, 2004

Related U.S. Application Data

(60) Provisional application No. 60/458,896, filed on Mar. 31, 2003.

(51) Int. Cl.
*G01R 1/06* (2006.01)
*G01R 1/067* (2006.01)

(52) U.S. Cl. ............... 324/664; 324/690; 324/347; 324/640

(58) Field of Classification Search ........ 324/664, 324/347, 644
See application file for complete search history.

(56) References Cited

U.S. PATENT DOCUMENTS

| 2,611,643 | A | | 9/1952 | Higgins |
| 3,905,551 | A | | 9/1975 | Lachevreliere |
| 4,481,474 | A | * | 11/1984 | Gerrit ..................... 324/425 |
| 5,450,012 | A | | 9/1995 | Champagne et al. |
| 5,479,104 | A | * | 12/1995 | Cambell ................. 324/690 |
| 6,401,742 | B1 | * | 6/2002 | Cramer et al. .......... 137/78.3 |
| 6,404,203 | B1 | * | 6/2002 | Lagmanson ............ 324/362 |
| 6,536,263 | B1 | * | 3/2003 | Wood et al. .............. 73/82 |
| 6,615,653 | B1 | * | 9/2003 | Hocking ............... 73/152.01 |

* cited by examiner

Primary Examiner—Andrew H. Hirshfeld
Assistant Examiner—John Zhu

(57) ABSTRACT

This disclosure describes a Soil Penetrating Electrode with Conical Taper for use with instrumentation for measurement of the electrical properties of soil in situ. The Electrode shape and configuration solves problems of stable and reliable contact with the soil, repeatable contact area, and ease of use by the operator.

2 Claims, 1 Drawing Sheet

SOIL PENETRATING ELECTRODE WITH CONICAL TAPER

CROSS-REFERENCE TO RELATED APPLICATIONS

Figure 1:
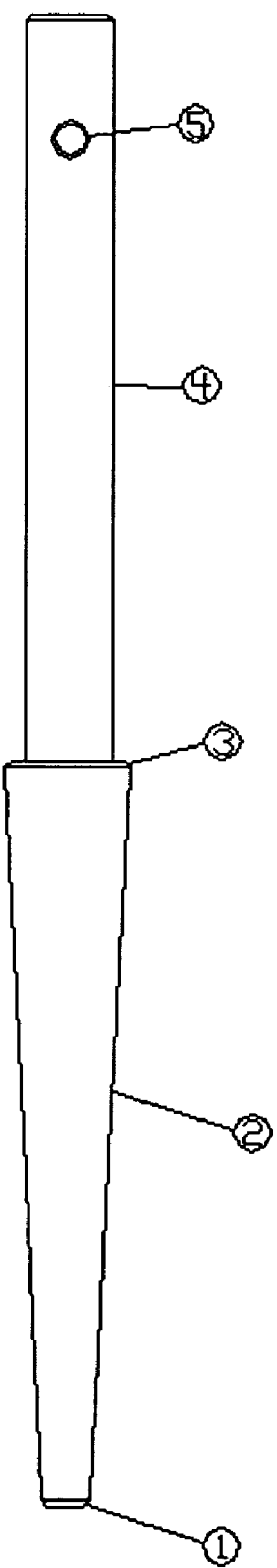

This application claims the benefit of provisional patent application Ser. No. 60/458,896, filed Mar. 31, 2003.

FEDERALLY SPONSORED RESEARCH

Not applicable

SEQUENCE LISTING OR PROGRAM

Not applicable

BACKGROUND OF THE INVENTION

1. Field of the Invention

The invention relates to the field of soil mechanics where measurement of soil percent compaction and moisture content are required for road beds and construction foundations. More particularly, the invention relates to the measurement of soil electrical resistance and soil electrical capacitance at a radio frequency, wherein electrodes are used to connect the measurement instrumentation to the soil.

2. Prior Art

There have been many applications wherein soil electrical properties have been measured to determine geological characteristics of soils and earth structures in situ. Generally the electrode structure has not been identified in the description of these inventions. U.S. Pat. No. 5,450,012, issued to Champagne, et. al. on Sep. 12, 1995, describes a Soil Electrode design that is claimed to be useful for determination the resistance of a volume of soil. Other prior art includes U.S. Pat. No. 2,611,643 of R. V. Higgins, granted on Sep. 23, 1952 that describes an automatic sprinkling device which includes two electrodes inserted into soil. U.S. Pat. No. 3,905,551 of Charles Ayme de la Lachevreliere, granted on Sep. 17, 1975 describes a soil sprinkling device employing two electrodes, one lying in the upper sprinkled layer, and the other lying within the permanently moist layer at sufficient depth.

OBJECTS AND ADVANTAGES

An object of this invention is to be able to make a repeatable and stable electrical contact with soil for measurement of its electrical properties.

Another object of this invention is to be able to control the area of electrical contact with soil for measurement of its electrical properties.

Yet another object of this invention is to be able to make it easy for the user to obtain repeatable and stable contact with soil for measurement of its electrical properties.

SUMMARY

The purpose of the Soil Penetrating Electrode with Conical Taper is to provide repeatable and stable electrical contact with soil for the purpose of measuring the electrical characteristics of the soil at a radio frequency. When used with the Electrical Density Gauge, the percent compaction and moisture content of the soil can be determined in situ from the measured electrical properties. It is important when making electrical measurements at radio-frequencies that the electrical contact area with the soil be constant so that best testing accuracy can be assured.

The Soil Penetrating Electrode with Conical Taper is made from metal that is hard enough to be hammered into the earth or soil, yet ductile enough to prevent shattering when hit. Typically, the composition of oil hardening drill rod is ideal for this application. The dimension of the Electrode is dependent upon the application requirements, and this description is intended to show an electrode suited to a typical application.

A conical shape has been designed for a soil penetrating electrode that continually compacts the soil around the electrode as it is driven in. This continual compaction achieves excellent contact all around the conical shape, and provides excellent control of the area of contact with the soil. Cylindrical electrode shapes can not be driven in to the soil manually with the precision needed to avoid side forces that would cause the hole to be oval shaped. A cylindrical electrode in an oval shaped hole has significantly less contact area than expected.

Further to controlling the contact area, a shoulder is machined at the end of the conical taper that is undercut. When the conical electrode is driven in the soil to the level where the shoulder is level with the soil surface, a repeatable area of the electrode is in contact with the soil.

If the electrode is driven farther into the soil, such that the shoulder is below the surface of the soil, the soil crumbs that may fall back in the cavity surrounding the undercut part of the electrode shaft make a comparatively poor contact with the electrode. Consequently, a negligible change results in the functional contact area of the electrode with the soil. Thus, the conical electrode shape that is the subject of this invention assures positive soil contact and substantially constant contact area without the requirement for highly accurate placement with respect to the soil surface.

DRAWINGS—FIGURES

FIG. 1 is a side view drawing of the Soil Penetrating Electrode with Conical Taper.

DETAILED DESCRIPTION—PREFERRED EMBODIMENT—FIG. 1

For this application, a 6 in. long Electrode is described, and detailed in FIG. 1. The length of the soil electrical contacting area (2) of the Electrode is three (3) inches. For best accuracy it is desirable that the total contact area be constant from measurement to measurement. It is also desirable that the Electrode be in intimate and tight electrical contact with the compacted soil. It is the object of this invention to solve the problem of constant electrical contact area and also to solve the problem of intimate electrical contact with the soil.

The point (1) of the Electrode has been blunted purposely to prevent distortion of the metal when a rock or large pebble is struck while placing the Electrode.

The contact area of the Electrode is machined to be a conical section (2) that has a diameter of 3/16 in. at the penetrating end (1), and a diameter of ½ in. at the top of the contact area (3). The conical taper is such that the spacing between the 3/16 in. dia. location and the ½ in. dia. location is 3 inches. As the Electrode is driven into the soil, the diameter of the hole continues to increase everywhere along its length, thus assuring intimate electrical contact.

The dimensions used in the above example result in a conical section that has a long, continuous small-angle taper of approximately 3.0 degrees.

At the ½ in. dia. location, a ¹⁄₁₆ in. shoulder (3) is machined, which reduces the diameter of the Electrode to ⅜ in. This shoulder provides a visual reference to assure that the Electrode is driven into the earth or soil, the full design distance of 3 in. From that point a ⅜ in. dia. cylindrical section (4) is machined for the remainder of the total 6 in. length of the Electrode. This cylindrical section provides a place to manually grip the Electrode while it is being driven into the soil, as well as a place to which electrical connectors can be affixed.

The cylindrical section (4) also provides an under-cut area, which no longer has intimate electrical contact with the soil or earth. Even if the Electrode is driven slightly deeper than the 3 in. design depth, the intimate electrical contact area will still be only 3 in. long. And, should any crumbs of earth fall into the undercut area, the relative electrical contact with the soil will be very small when compared with the tight electrical contacting area of the conical section Lastly, a hole (5) is drilled transversely through the top area of the cylindrical section of the Electrode through which a rod or nail can be inserted to permit the electrode to be twisted as it is pulled from the earth or soil after use. This feature permits easy withdrawal of the Electrode, when driven into highly compacted soils.

CONCLUSION, RAMIFICATIONS, AND SCOPE

Accordingly the reader will see that I have provided a new and novel Electrode shape that solves several problems associated with the need for constant contact area when making radio frequency electrical measurement of soil parameters, the need for convenience related to the ease of controlling penetration depth, and for ease of removal.

The term soil is used generically, and can include compactable construction material, and other compactable foundation and road bed materials.

The conductive metallic soil penetrating electrode can be made from steel, stainless steel, bronze, or other metal with suitable electrical conductance for the application.

The above description of the conical electrode includes typical dimensions, which may change according to the soil type and application of this new electrode shape.

The taper angle of the electrode conical section may be larger or smaller than 3.0 degrees so as to optimize intimate contact with the soil in special applications.

It will be seen that the conductive metallic soil penetrating electrode is useful for making an electrical connection with soil for the purpose of measuring soil electrical parameters, and comprises:

a) said electrode having an axially longitudinally elongated body defining first and second integral sections, the first section having ground engaging slim taper along the majority of its length, the second section being substantially cylindrical along the majority of its length, b) said first section having a primary end defining a tip, and a secondary end forming a shoulder which extends outwardly away from a junction defined by said section, c) said first section at said junction having an overall cross dimension which exceeds the diameter of said second section proximate the junction, the ratio of said overall cross dimension to said second section diameter being about 4/3, d) said electrode configured to receive radio frequency energy at said second section, e) said tip being blunted to define a flat end and a shallowly tapered periphery, and having a diameter of about ³⁄₁₆ inch.

I claim as the subject of my invention:

1. A conductive metallic soil penetrating electrode for use in making an electrical connection with soil for the purpose of measuring soil electrical parameters comprising in combination:

a) said electrode having an axially longitudinally elongated body defining first and second integral sections, the first section having ground engaging slim taper along the majority of its length, the second section being substantially cylindrical along the majority of its length, b) said first section having a primary end defining a tip, and a secondary end forming a shoulder which extends outwardly away from a junction defined by said sections, c) said first section at said junction having an overall cross dimension which exceeds the diameter of said second section proximate the junction, the ratio of said overall cross dimension to said second section diameter being about 4/3, d) said electrode configured to receive radio frequency energy at said second section, e) said tip being blunted to define a flat end and a shallowly tapered periphery, and having a diameter of about ³⁄₁₆ inch, f) said overall cross dimension is about ½ inch, g) said first section has an overall length of approximately 3 inches, h) said taper is approximately 3.0 degrees, i) the diameter of the second section proximate the junction is approximately ⅜ inch, j) the diameter of the second section along the majority of its length is approximately ⅜ inch, k) the second section has a length of approximately 3 inches, l) the overall length of the electrode is approximately 6 inches, m) said second section has a cylindrical surface locus to which the electrical connector is applied, n) the first section is driven into the earth to a level proximate said junction.

2. The electrode of claim 1 further characterized by the following:

o) said flat end defining the major extent of said tip.

* * * * *